United States Patent
Wang et al.

(10) Patent No.: US 10,935,551 B2
(45) Date of Patent: Mar. 2, 2021

(54) ULTRA-HIGH SENSITIVITY DUAL-GATED BIOSENSOR BASED ON MOS TRANSISTOR

(71) Applicant: Wuxi People's Hospital, Wuxi (CN)

(72) Inventors: Tong Wang, Wuxi (CN); Yanfeng Jiang, Wuxi (CN); Ye Zhang, Wuxi (CN); Hang Chen, Wuxi (CN); Jialin Sun, Wuxi (CN); Hang Li, Wuxi (CN)

(73) Assignee: WUXI PEOPLE'S HOSPITAL, Wuxi (CN)

( * ) Notice: Subject to any disclaimer, the term of this patent is extended or adjusted under 35 U.S.C. 154(b) by 13 days.

(21) Appl. No.: 16/482,266

(22) PCT Filed: Nov. 1, 2018

(86) PCT No.: PCT/CN2018/113289
§ 371 (c)(1),
(2) Date: Jul. 31, 2019

(87) PCT Pub. No.: WO2019/096011
PCT Pub. Date: May 23, 2019

(65) Prior Publication Data
US 2019/0346447 A1    Nov. 14, 2019

(30) Foreign Application Priority Data
Nov. 20, 2017   (CN) .......................... 201711157594.7

(51) Int. Cl.
*G01N 33/551*    (2006.01)
*G01N 33/574*    (2006.01)
(Continued)

(52) U.S. Cl.
CPC ..... *G01N 33/57473* (2013.01); *G01N 27/227* (2013.01); *G01N 33/54373* (2013.01);
(Continued)

(58) Field of Classification Search
None
See application file for complete search history.

(56) References Cited

U.S. PATENT DOCUMENTS

2006/0166415 A1    7/2006   Afentakis et al.

FOREIGN PATENT DOCUMENTS

CN      101592627 A      12/2009
CN      102435655 A      5/2012
(Continued)

*Primary Examiner* — Christopher L Chin
(74) *Attorney, Agent, or Firm* — Bayramoglu Law Offices LLC

(57) ABSTRACT

An ultra-high sensitivity dual-gated biosensor based on an MOS transistor, which is applicable to detection of a series of early tumors. The sensor is prepared and processed by using SOI wafers, and a unique dual-gated structure is realized by ion implantation technique. The sensor is prepared by an ultraviolet lithography combined with an NLD etching method, realizing trace, instant and marker-free detection of tumor markers. The method detects a change in capacitance in the channel during binding of antigen antibodies. The detection method involved in the invention is more stable and strong in anti-interference, can meet the demands in the aspect of detection range and sensitivity, and especially has extremely outstanding detection sensitivity, and can detect a sample with a lowest concentration in the range of 1 fg/ml~1 ng/ml.

8 Claims, 4 Drawing Sheets

(51) Int. Cl.
  *G01N 27/22* (2006.01)
  *H01L 21/02* (2006.01)
  *H01L 21/027* (2006.01)
  *H01L 21/265* (2006.01)
  *H01L 21/266* (2006.01)
  *H01L 21/28* (2006.01)
  *H01L 21/285* (2006.01)
  *H01L 21/3065* (2006.01)
  *H01L 21/308* (2006.01)
  *G01N 33/543* (2006.01)

(52) U.S. Cl.
  CPC ..... *G01N 33/57476* (2013.01); *H01L 21/022* (2013.01); *H01L 21/0217* (2013.01); *H01L 21/02057* (2013.01); *H01L 21/0274* (2013.01); *H01L 21/02164* (2013.01); *H01L 21/02238* (2013.01); *H01L 21/02274* (2013.01); *H01L 21/02532* (2013.01); *H01L 21/02603* (2013.01); *H01L 21/266* (2013.01); *H01L 21/26513* (2013.01); *H01L 21/28079* (2013.01); *H01L 21/28194* (2013.01); *H01L 21/28568* (2013.01); *H01L 21/308* (2013.01); *H01L 21/3065* (2013.01)

(56) References Cited

FOREIGN PATENT DOCUMENTS

| | | |
|---|---|---|
| CN | 102951591 A | 3/2013 |
| CN | 103558279 A | 2/2014 |
| CN | 107328838 A | 11/2017 |
| CN | 108169485 A | 6/2018 |

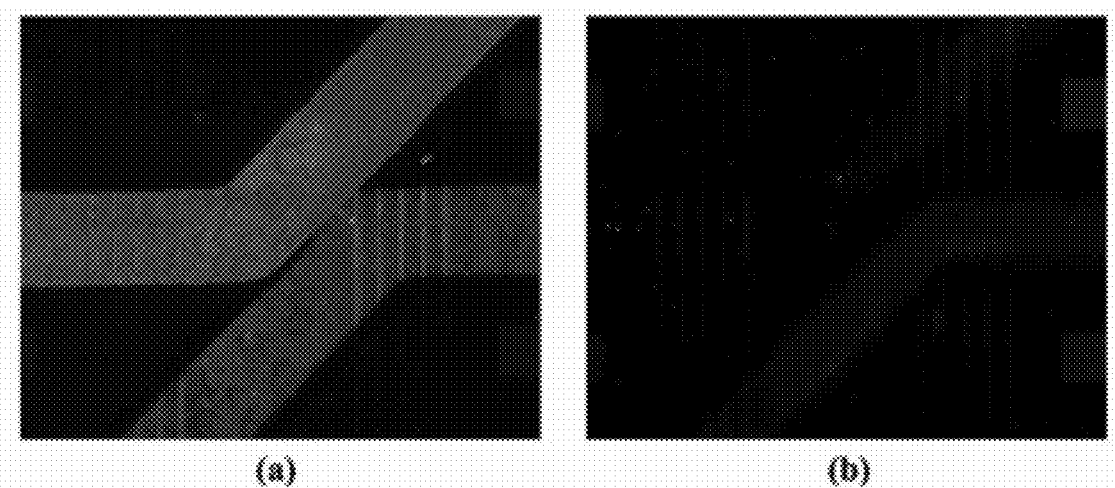
FIG. 3
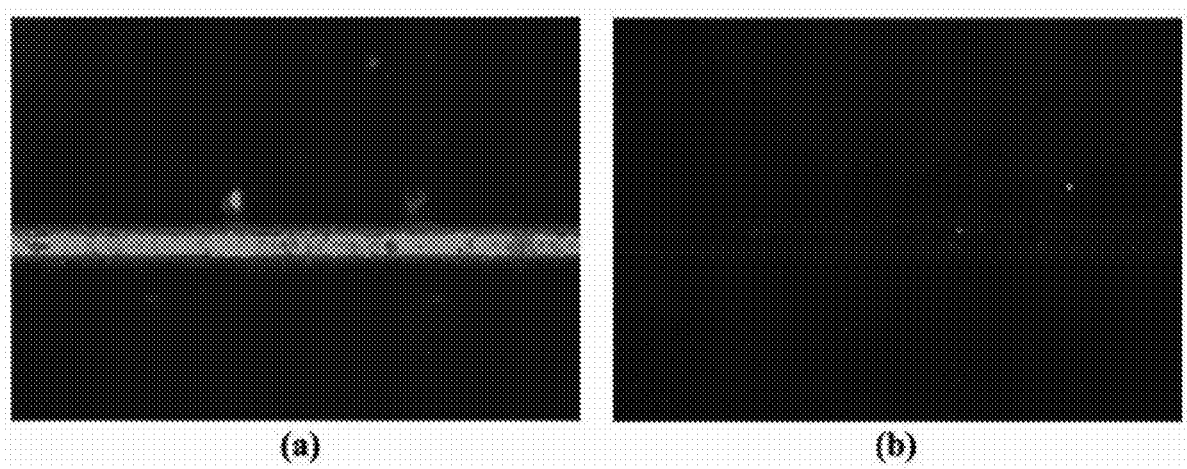
FIG. 4
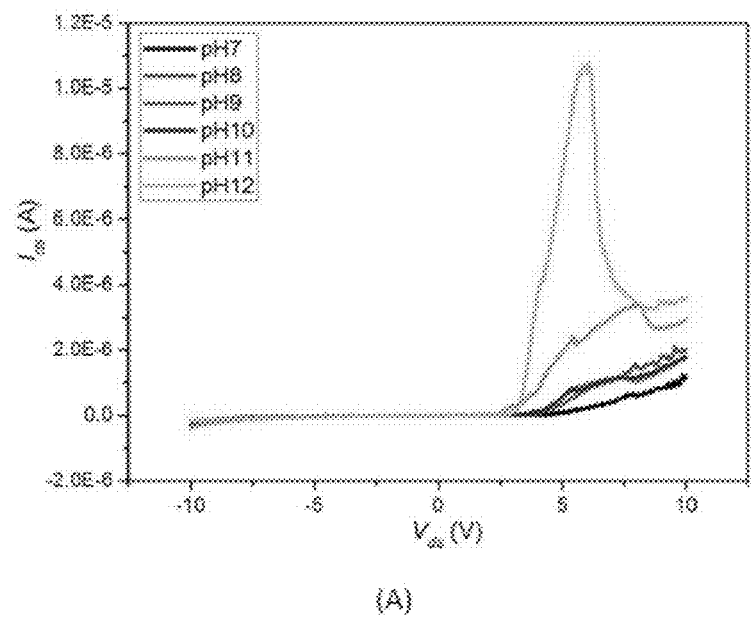
(A)

(B)

ULTRA-HIGH SENSITIVITY DUAL-GATED BIOSENSOR BASED ON MOS TRANSISTOR

CROSS REFERENCE TO RELATED APPLICATIONS

This application is the national phase entry of International Application No. PCT/CN2018/113289, filed on Nov. 1, 2018, which is based upon and claims priority to Chinese Patent Application No. 201711157594.7, filed on Nov. 20, 2017, the entire contents of which are incorporated herein by reference.

TECHNICAL FIELD

The present invention relates to the technical field of biological material detection, and in particular to high-success-rate preparation and application methods of an ultra-high sensitivity biosensor based on a metal oxide semiconductor (MOS) transistor.

BACKGROUND

Malignant tumor is one of major diseases that currently threaten human health, however, most tumors develop clinical manifestations in advanced stages, and therefore, an early, quick, and sensitive diagnosis of a malignant tumor is an important means to improve human survival quality. Currently, the clinical tumor pathogenesis monitoring method mainly relies on imageological examination and detection of tumor markers. It is often not possible for the imageological examination to do long term follow-up due to resolution and radiation risks thereof. Although detection of tumor markers is simple and convenient to operate, the sensitivity and specificity of tumor marker detection become important factors limiting its application. Therefore, finding a simple and accurate detection method for the risk diagnosis and early diagnosis of tumor incidence has become an important research direction to improve human survival quality.

Currently, a detection method of tumor markers used widely in clinical treatment is a classical ELISA method, however, its clinical application is limited to a certain extent due to high requirements of the detection environment, strong detection subjectivity, low sensitivity and the like. The rapid development of nanometer (nanometer, nm) technology brings a new idea for the detection method of tumor markers. The biosensor based on an MOS (metal oxide semiconductor) transistor can directly convert the binding of target molecules and the surface of the device into electrical signals, and thus has a great significance for improving human survival quality as a sensor with good sensitivity and specificity.

SUMMARY

Technical Problem

However, as for the traditional process for preparing silicon nanoribbon by wet etching, the uncontrollability of the etching rate results in unstable performance of the device, and the width of the obtained silicon nanoribbon is uncontrollable, significantly increasing the cost and thus limiting the wide application of an ultra-high sensitivity biosensor to a great extent. Therefore, it has an important application value to develop high-success-rate preparation of an ultra-high sensitivity biosensor.

Technical Solution

In view of the above problems existing in the prior art, the application provides an ultra-high sensitivity dual-gated biosensor based on an MOS transistor. The first object of the present invention is to provide a preparation method of an ultra-high sensitivity biosensor based on a MOS transistor, rapid and efficient detection of tumor related markers is realized on the basis of improving the traditional sensor processing technology, the operation is simple, and the cost is low. The second object of the present invention is to provide an application of the biochip described above.

The working principle of the present sensor is related to the specific binding among antigen antibodies via a linker chain; the change in electrical signals caused by the specific binding can be captured by an electrical test system connected to the probe station, so that low concentration and instant detection of tumor markers in the sample can be realized; the sample can be whole blood, serum, or buffer solution.

The technical solutions of the present invention are described as follows:

A biosensor based on an MOS transistor, including a detection system and a micro-channel system bonded to each other, wherein the detection system includes a substrate (8) and an ion implantation layer (7) tiled above the substrate (8); two groups of opposed U-shaped electrode pairs are arranged on the ion implantation layer (7); two wings of the U-shaped electrode pair are source and drain electrodes (1) and (4), a top gate (3) is connected to the bottom of the U-shaped electrode pairs, and a surface gate (2), parallel to the top gate (3) and not connected to the U-shaped electrode pair, is provided within the U-shaped electrode pair;

the source and drain electrodes (1) and (4) are in turn made up of a silicon layer (10), an oxide layer (9) and a metal layer (6) above the ion implantation layer (7);

silicon nanowires (5) are connected to the source and drain electrodes (1) and (4) at the bottom of the U-shaped electrode; the silicon nanowire (5) is constructed by ultraviolet lithography and neutral loop discharge (NLD) etching; the silicon nanowire (5) has a length from 10 nm to 100 um, a width from 10 nm to 5 um, and a thickness from 10 nm to 500 nm;

the two-wing source and drain electrodes (1) and (4), the surface gate (2) and the top gate (3) of the U-shaped electrode pair are all wrapped with a passivation layer (11), and only the ends of all the electrodes and the gates and silicon nanowires (5) are exposed.

The applicant also provides a preparation method of a biosensor based on a MOS transistor, including the steps of:

(I) preparing a detection system;
(II) preparing a micro-channel;
(III) bonding the detection system and the micro-channel system.

Step (I) includes the following procedures:

A. surface silicon thinning: cleaning silicon wafer, and performing high-temperature oxidation at 900-1100° C. for 1-10 hours in an oxidation furnace by dry oxidation-wet oxidation-dry oxidation; then rinsing with buffered oxide etch (BOE) to remove the $SiO_2$ layer, and reducing the surface silicon to 10-100 nm to obtain a silicon layer (10);

B. preparation of silicon nanowires (5): exposing and developing using an ultraviolet stepper aligner to obtain a nanowire pattern, plating a layer of chromium with a thickness of 10-1000 nm as a mask on a pattern region by magnetron sputtering, and etching integrally using an NLD etching method to remove Si and $SiO_2$ in a non-pattern region and expose the substrate (8);

C. ion implantation: performing full-layer ion implantation to conduct an exposed substrate (8) and preparing for later lead-out of the surface gate (2); the implanted ions are nitrogen, phosphorus or arsenic As, with an implantation dose of 1e14-1e20/$cm^2$, and an implantation energy of 10 keV-1 MeV, to obtain an ion implantation layer (7);

D. construction of the oxidation layer (9) on the silicon nanowire (5): growing $SiO_2$ with a thickness of 1-100 nm on a partial region of the silicon nanowire (5) by an MA6 ultraviolet lithography device and plasma enhanced chemical vapor deposition (PECVD), and preparing for later lead-out of the top gate (3);

E. preparation of the source electrode (1), the drain electrode (4), the surface gate (2) and the top gate (3) patterns: uniformly coating a layer of photoresist on the surface of an silicon-on-insulator (SOI) silicon wafer, preparing patterns of the source electrode (1), the drain electrode (4), the surface gate (2) and the top gate (3) at specific positions by using an ultraviolet lithography method, depositing Ti/Au/Ti trilayer metal, i.e., the metal layer (6) on the surface of the substrate (8) by thin film deposition techniques, the thicknesses are selected from 1-10 nm/10-200 nm/1-10 nm, and finally stripping to obtain the electrode pattern;

F. preparation of ohmic contact: rapidly raising the temperature to 350-500° C. with a rapid annealing furnace under the protection of nitrogen, maintaining for 1-100 seconds and then lowering the temperature, and establishing ohmic contact between the electrode and the silicon nanowire (5);

G. preparation of the passivation layer (11): uniformly coating a layer of an electron beam photoresist on the surface of the SOI silicon wafer of the substrate (8), preparing the passivation layer with an ultraviolet lithography method, depositing a double-layered $SiO_2/SiN_x$ thin film on the surface of the substrate (8) by thin film deposition techniques, the thicknesses are selected from 10-1000 nm/10-500 nm, and obtaining the passivation layer (11) in combination with a peel-off technique. The thin film deposition techniques can adopt magnetron sputtering. The passivation layer (11) is to prevent electric leakage.

Step (II) includes the following procedures:

A. successively applying ultrasonic cleaning to the silicon wafer with acetone, isopropanol and ultrapure water each for 5-15 minutes, coating a layer of photoresist on the surface using a glue leveling platform, with a coating thickness of 2-10 μm, obtaining a micro-channel photoresist pattern by ultraviolet lithography; and etching on the silicon wafer using deep silicon etching, with an etching depth of 100-150 μm;

B. performing fluorosilane treatment on the silicon wafer, so that the surface possesses a superhydrophobic property to facilitate subsequent peel-off of micro-channel materials; coating polydimethylsiloxane PDMS or SU-8 photoresist on the surface of the silicon wafer and performing curing treatment; and peeling the PDMS off the surface of the silicon wafer after curing;

C. punching on the surface of the PDMS or the SU-8 photoresist with a puncher to obtain an inlet and an outlet of the micro-channel, wherein the region between the two is a passage in the micro-channel system.

Step (III) includes the following procedures:

performing surface treatment on the substrate (8) of the micro-channel system and the detection system with an oxygen plasma system to obtain a superhydrophilic surface, and then aligning and bonding the two to complete the preparation of the biosensor.

The material of the micro-channel is polydimethylsiloxane PDMS or SU-8 photoresist.

The applicant also provides a method of detecting a tumor marker using the biosensor described above, including the following steps:

A. modifying antibody protein: connecting a micro-channel passage, passing and residing 1-1000 m/ml of antibodies at a normal temperature by means of a syringe pump or a peristaltic pump on the surface of the silicon nanowire (5), wherein the modification time is less than 0.1 to 10 hours; and subsequently cleaning the biosensor with immunostaining washings/a phosphate buffered saline Polysorbate-20 (PBST) solution and blowing dry with nitrogen, wherein the purpose of such operations is to modify the corresponding antibody of a target tumor marker on the silicon nanowire (5) of the biosensor;

B. analyzing: after fixing, pricking and passage-connecting operations are completed on a probe station, passing a phosphate buffered saline (PBS) solution through the micro-channel system for 1 to 100 minutes at a flow rate of 0.001-100 ml/min by means of a syringe pump or a peristaltic pump to obtain a base current value, and then slowly conveying a sample to be detected to a silicon nanowire (5) region of the biosensor and staying for several minutes, so that the target tumor marker in the sample to be detected is sufficiently bound with the antibody protein, and continuously conveying the solution to an outlet of the micro-channel by means of a syringe pump or a peristaltic pump;

C. detecting: during the conveying process, capturing, by an electrical analyzer using a C-V mode, changes in electrical signals relative to the baseline.

The tumor marker includes α-fetoprotein AFP and carcinoembryonic antigen CEA tumor markers.

The present invention adopts a brand-new tumor detection method, compared to the C-V method, the method has advantages of being simple and convenient, highly sensitive, and resistant to strong interference. This method detects a change in capacitance in the channel during binding of antigen antibodies. For example, when the antibody binds to a negatively charged antigen protein, the total charge numbers accumulated in the channel increases due to charge adsorption, and ultimately results in an increase in capacitance with a given area of a nanoribbon. Compared to other electrical signals, the capacitance value is more stable, and can detect a smoother curve, can obtain a good detection result even if not in an electromagnetic shield box, and can detect a sample with a lowest concentration in the range of 1 fg/ml~1 ng/ml in terms of sensitivity.

The silicon nanoribbon in the present invention is prepared by an ultraviolet lithography combined with an NLD etching method. Compared with a traditional wet etching process, the roughness, the width and the success rate of the nanowires are greatly improved. The metal of the source electrode, the drain electrode and the dual-gate is Ti/Au/Ti trilayer metal, and the rapid annealing conditions are that: the temperature is rapidly raised to 350-500° C., maintained for 1-100 seconds or so and then lowered, so that wire-breakage rate of the silicon nanoribbon in the annealing process can be greatly reduced. The passivation layer is prepared by using an ultraviolet lithography method in combination with a peel-off technique, so that damage to a chip not controllable in the traditional process can be avoided. Therefore, the processing and use cost of the biosensor based on an MOS (metal oxide semiconductor) transistor can be directly reduced.

By adopting the biosensor based on an MOS (metal oxide semiconductor) transistor, the present invention can directly convert the binding of a variety of target molecules and the surface of the device into electrical signals, exhibit excellent sensitivity and specificity, meanwhile achieve multi-marker detection of a single sample, and thus have a great significance for improving human survival quality. Meanwhile, the introduction of the dual-gate greatly improves the regulation and control effect of a gate voltage on source and drain currents, and enhances the sensitivity of the device.

The biochip according to the present invention is applicable to whole blood samples, and can avoid loss of tumor markers due to the sample pretreatment process and thus meet subsequent detection application demands.

wherein, 1, 4: source and drain electrodes, 2: a surface gate, 3: a top gate, 5: a nanowire, 6: a metal layer, 7: an ion implantation layer, 8: a substrate, 9: an oxide layer, 10: a silicon layer; a passivation layer 11 is not shown.

Figure 2:
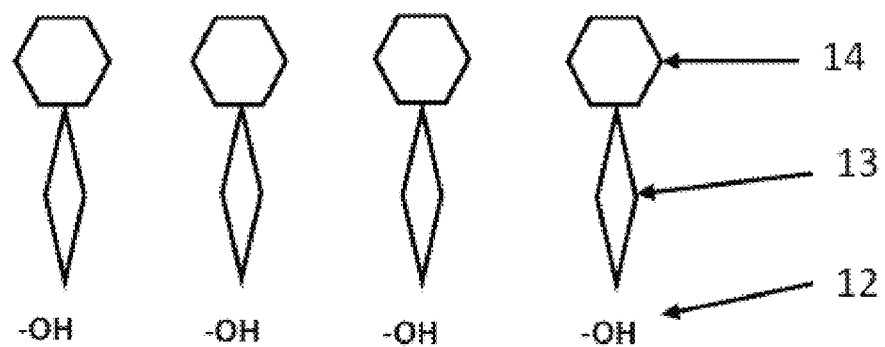
Figure 2:
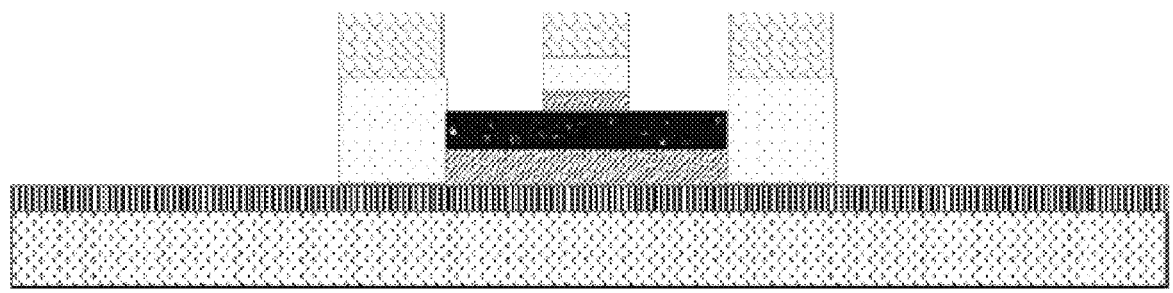

FIG. 2 is a schematic diagram of a silicon nanoribbon surface antibody modification: 13—a hydroxyl group (OH), 14—a linker chain, 15—an antibody corresponding to a tumor marker.

FIG. 3 is a schematic diagram illustrating micro-channel modification effects; wherein (a) is that a device is synchronously modified with a green fluorescent protein and a red fluorescent protein, respectively, through a micro-channel system; (b) is that small amounts of non-specific adsorption of the red fluorescent protein can be seen for the negative reference only after simply passing through the fluorescent protein.

FIG. 4 shows non-specific adsorption after the micro-channel system passes through the green fluorescent protein; wherein (a) shows non-specific adsorption after a micro-channel system not blocked with BSA passes through the green fluorescent protein; (b) shows non-specific adsorption after a micro-channel system blocked with BSA passes through the green fluorescent protein.

Figure 5:
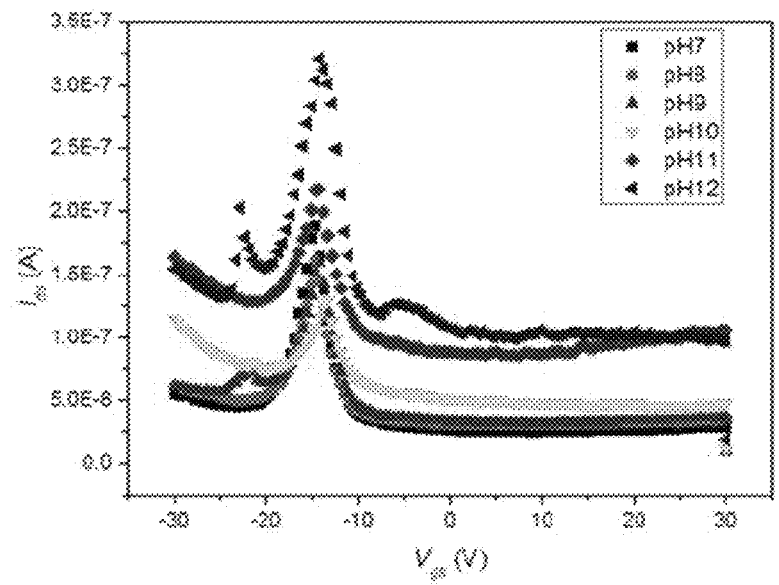

FIG. 5 shows a real-time detection of the present sensor for output transfer signals in solutions with different pH values.

Figure 6:
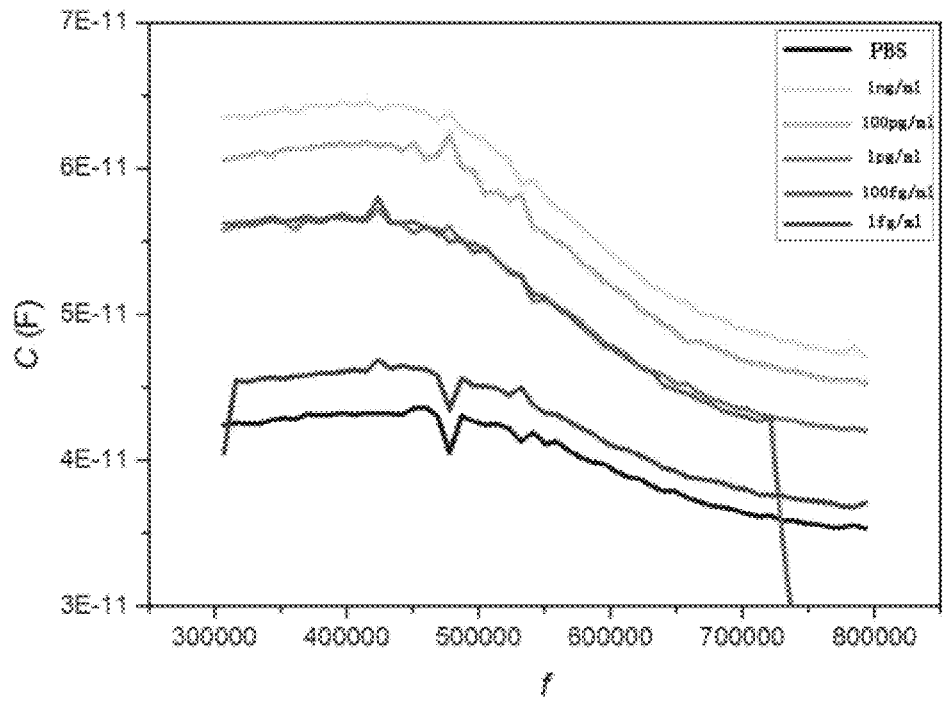

FIG. 6 is a real-time monitoring of the present sensor for different concentrations of AFP in serum.

Figure 7:
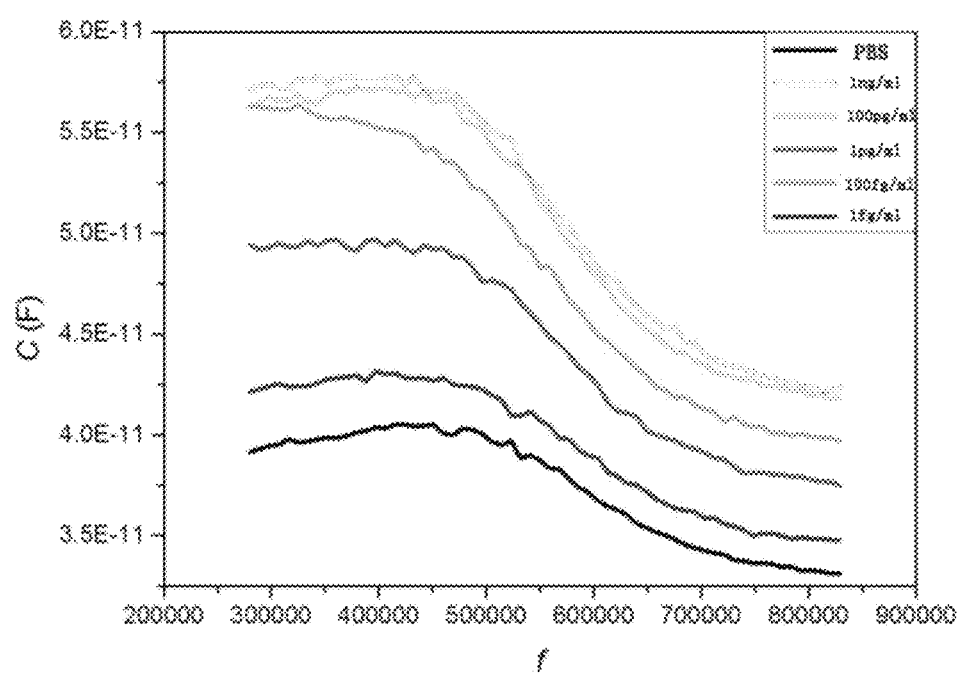

FIG. 7 is a real-time monitoring of the present sensor for different concentrations of CEA in serum.

DETAILED DESCRIPTION OF THE EMBODIMENTS

Embodiment 1: Preparation of Sensor According to the Present Invention

Figure 1:
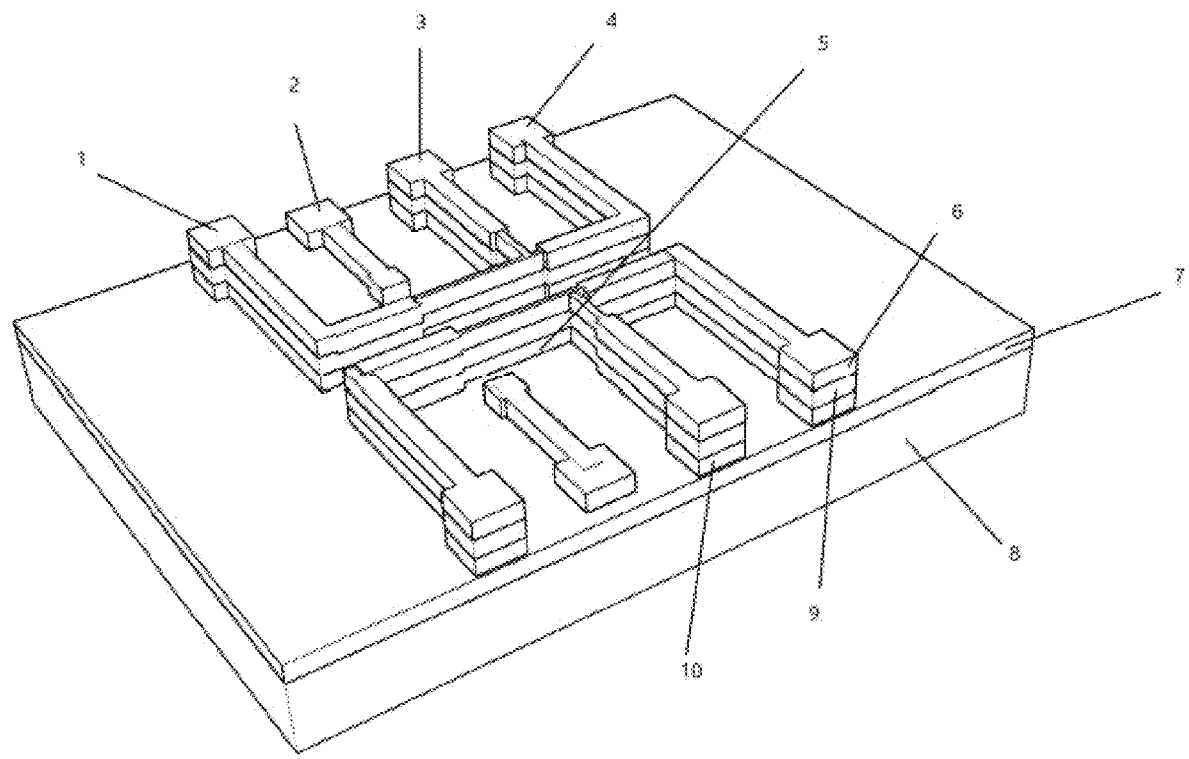
FIG. 1 is a structural diagram of an ultra-high sensitivity dual-gated biosensor based on an MOS transistor.

As shown in FIG. 1, the present invention provides a biosensor based on an MOS transistor, including a detection system and a micro-channel system bonded to each other, wherein the detection system includes a substrate 8 and an ion implantation layer 7 tiled above the substrate 8; two groups of opposed U-shaped electrode pairs are arranged on the ion implantation layer 7; two wings of the U-shaped electrode pair are source and drain electrodes 1,4, a top gate 3 is connected to the bottom of the U-shaped electrode pairs, and a surface gate 2, parallel to the top gate 3 and not connected to the U-shaped electrode pair, is provided within the U-shaped electrode pair;

the source and drain electrodes 1,4 and the top gate 3 are in turn made up of a silicon layer 10, an oxide layer 9 and a metal layer 6 above the ion implantation layer 7;

silicon nanowires 5 are connected to the source and drain electrodes 1 and 4 at the bottom of the U-shaped electrode; the silicon nanowire 5 is constructed by ultraviolet lithography and NLD etching; the silicon nanowire 5 has a length from 10 nm to 100 um, a width from 10 nm to 5 um, and a thickness from 10 nm to 500 nm;

the two-wing source and drain electrodes 1 and 4, the surface gate 2 and the top gate 3 of the U-shaped electrode pair are all wrapped with a passivation layer 1 (not shown in FIG. 1), and only the ends of all the electrodes and the gates and silicon nanowires 5 are exposed.

The present invention provides a preparation method of a biosensor based on a MOS transistor, including the steps of:

(I) Preparing a Detection System;

A. surface silicon thinning: cleaning silicon wafer, and performing high-temperature oxidation at 900-1100° C. for 1-10 hours in an oxidation furnace by dry oxidation-wet oxidation-dry oxidation; then rinsing with BOE to remove the $SiO_2$ layer, and reducing the surface silicon to 10-100 nm to obtain a silicon layer 10;

B. preparation of silicon nanowires 5: successively applying ultrasonic cleaning to the silicon wafer with acetone, isopropanol and ultrapure water each for 5-15 minutes, exposing and developing using an ultraviolet stepper aligner to obtain a nanowire pattern, plating a layer of chromium with a thickness of 10-1000 nm as a mask on a pattern region by magnetron sputtering, and etching integrally using an NLD etching method to remove Si and $SiO_2$ in a non-pattern region and expose the substrate 8;

C. ion implantation: performing full-layer ion implantation to conduct an exposed substrate 8 and preparing for later lead-out of the surface gate 2; the implanted ions are nitrogen, phosphorus or arsenic As, with an implantation dose of 1e14-1e20/cm$^2$, and an implantation energy of 10 keV-1 MeV, to obtain an ion implantation layer 7;

D. construction of the oxidation layer 9 on the silicon nanowire 5: growing $SiO_2$ with a thickness of 1-100 nm on a partial region of the silicon nanowire 5 by an MA6 ultraviolet lithography device and PECVD, and preparing for later lead-out of the top gate 3;

E. preparation of the source electrode 1, the drain electrode 4, the surface gate 2 and the top gate 3 patterns: uniformly coating a layer of photoresist on the surface of an SOI silicon wafer, preparing patterns of the source electrode 1, the drain electrode 4, the surface gate 2 and the top gate 3 at specific positions by using an ultraviolet lithography method, depositing Ti/Au/Ti trilayer metal, i.e., the metal layer 6 on the surface of the substrate 8 by thin film deposition techniques, the thicknesses are selected from 1-10 nm/10-200 nm/1-10 nm, and finally stripping to obtain the electrode pattern;

F. preparation of ohmic contact: rapidly raising the temperature to 350-500° C. with a rapid annealing furnace under the protection of nitrogen, maintaining for 1-100 seconds and then lowering the temperature, and establishing ohmic contact between the electrode and the silicon nanowire 5;

G. preparation of the passivation layer 11: uniformly coating a layer of an electron beam photoresist on the surface of the SOI silicon wafer of the substrate 8, preparing the passivation layer with an ultraviolet lithography method, depositing a double-layered $SiO_2/SiN_x$ thin film on the surface of the substrate 8 by thin film deposition techniques, the thicknesses are selected from 10-1000 nm/10-500 nm, and obtaining the passivation layer 11 in combination with a peel-off technique. The thin film deposition techniques can adopt magnetron sputtering.

The substrate 8 of the biosensor adopts an SOI silicon wafer.

(II) Preparing a Micro-Channel System.

A. successively applying ultrasonic cleaning to the silicon wafer with acetone, isopropanol and ultrapure water each for 5-15 minutes, coating a layer of photoresist on the surface using a glue leveling platform, with a coating thickness of 2-10 μm, obtaining a micro-channel photoresist pattern by ultraviolet lithography; and etching on the silicon wafer using deep silicon etching, with an etching depth of 100-150 μm;

B. performing fluorosilane treatment on the silicon wafer, so that the surface possesses a superhydrophobic property to facilitate subsequent peel-off of micro-channel materials; coating polydimethylsiloxane PDMS or SU-8 photoresist on the surface of the silicon wafer and performing curing treatment; and peeling the PDMS off the surface of the silicon wafer after curing;

C. punching on the surface of the PDMS or the SU-8 photoresist with a puncher to obtain an inlet and an outlet of the micro-channel, wherein the region between the two is a passage in the micro-channel system.

(III) Integrating the Detection System and the Micro-Channel System:

A. construction of a linker chain: firstly, putting the detection system subjected to oxygen plasma treatment for 1-10 min into 1-10 wt % of APTES anhydrous ethanol solution to react for 1-100 min, and heating for 0.1-10 h at 80-200° C. after blowing dry with nitrogen, then putting into 1-10 wt % of glutaraldehyde deionized aqueous solution to react for 0.1-10 hours, and blowing dry with nitrogen;

B. sealing of PDMS or SU-8 micro-channel and the detection system: carrying out oxygen plasma treatment on the cleaned PDMS or SU-8 micro-channel for 1-10 min to obtain a superhydrophilic surface, and then immediately performing irreversible bonding with the detection system to complete the preparation of the biosensor.

FIG. 2 shows a schematic diagram of antibody protein and biosensor modification, wherein, 14 is an antibody protein, and 13 represents a series of linker chains, 12 is an OH— on the surface of the sensor after being subjected to oxygen plasma treatment, and it can be found that, the antibody protein is firmly bound with the biosensor through a chemical linker chain.

In order to verify the overall modification effect of such a micro-channel structure, firstly, the micro-channel is sealed on the surface of the device by irreversible sealing, the surface of the device is synchronously modified with a green fluorescent protein and a red fluorescent protein, respectively, through a micro-channel system, it can be seen that no leakage occurs between the two micro-channels, and meanwhile, the surface of the device is well modified by the green fluorescent protein and the red fluorescent protein, as shown in FIG. 3.

Blocking effect of BSA on the micro-channel system: FIG. 4 shows non-specific protein adsorption result of the micro-channel system blocked with BSA by means of the green fluorescent protein detection, it can be found, non-specific adsorption of the blocked micro-channel system on proteins is reduced obviously.

According to the above method, the success rate of preparing the biosensor based on an MOS transistor is over 90%.

Embodiment 2: Trace, Instant Detection of α-Fetoprotein (AFP), Carcinoembryonic Antigen (CEA)

Detection is Conducted in the Following Manner:

A. modifying antibody protein: connecting a micro-channel passage, passing and residing 1-1000 μg/ml of antibodies at a normal temperature by means of a syringe pump or a peristaltic pump on the surface of the silicon nanowire 5, wherein the modification time is less than 0.1 to 10 hours; and subsequently cleaning the biosensor with immunostaining washings/a PBST solution and blowing dry with nitrogen, wherein the purpose of such operations is to modify the corresponding antibody of a target tumor marker on the silicon nanowire 5 of the biosensor;

B. analyzing: after fixing, pricking and passage-connecting operations are completed on a probe station, passing a PBS solution through the micro-channel system for 1 to 100 minutes at a flow rate of 0.001-100 ml/min by means of a syringe pump or a peristaltic pump to obtain a base current value, and then slowly conveying a sample to be detected to a silicon nanowire 5 region of the biosensor and staying for several minutes, so that the target tumor marker in the sample to be detected is sufficiently bound with the antibody protein, and continuously conveying the solution to an outlet of the micro-channel by means of a syringe pump or a peristaltic pump;

C. detecting: during the conveying process, capturing, by an electrical analyzer using a C-V mode, changes in electrical signals relative to the baseline. The tumor marker includes α-fetoprotein AFP and carcinoembryonic antigen CEA tumor markers.

FIG. 5 shows the detection of a nanodevice in solutions with different pH values. It can be seen that, an ultra-high sensitivity biosensor based on an MOS transistor can stably make instant response to solutions with different pH values. At the same time, serum samples containing different concentrations of AFP and CEA are studied and detected to obtain the following curves (FIG. 6 and FIG. 7). As can be seen from the curves, as the concentration of the detected sample gradually increases, the detected capacitance value also has a significant ascending trend, and the detection range is as low as 1 fg/ml to 1 ng/ml, spanning six orders of magnitude.

Currently, detection of a clinically common series of tumor markers have been achieved by the present invention, among the diseases including AFP, CEA, CA125, PSA, β2-MG, NES, SCC and the like, the diseases involved include a series of tumors of liver cancer, gastric cancer, colorectal cancer, breast cancer, lung cancer, cervical cancer and the like.

It should be noted that, all of these detections are conducted under whole blood conditions. It is well known that the whole blood has extremely complex composition, including a variety of proteins, lipids, amino acids and buffer ions, and the like, which has a dramatic effect on the results of detection. The present invention mainly addresses the aforementioned difficulties through a bio-molecular enrichment system that can purify antigen proteins which we need from whole blood, so as to achieve efficient detection. The working principle of the invention is to use customized photo-cracking magnetic beads, which can adsorb antigen proteins in the whole blood, then centrifuge and remove the supernatant to obtain precipitated magnetic beads with the antigen, and finally separate the antigen proteins and the photo-cracking magnetic beads with an illumination method. Such a bio-molecular enrichment system will be described in detail in our additional patent and is not repeated herein.

The above description is merely preferred embodiments of the present invention, and is not intended to limit the present invention in any form. Although the preferred embodiments according to the present invention are disclosed as foregoing, they are not intended to limit the invention. It should be noted that for persons skilled in the art, the technical solutions of the invention may be improved and modified or be changed as equivalent embodiments by use of the above-disclosed methods and technical contents without departing from the scope of the technical solutions of the present invention. Therefore, any simple improvement, equivalent change and modification made to the above embodiment according to the technical substantive contents of the present invention without departing from the contents of the technical solutions of the present invention, falls into the protection scope of the technical solutions of the present invention.

What is claimed is:

1. A biosensor based on an MOS transistor, comprising: a detection system and a micro-channel system bonded to each other, wherein the detection system comprises a substrate and an ion implantation layer tiled above the substrate; wherein, two groups of opposed U-shaped electrode pairs are arranged on the ion implantation layer; two wings of each U-shaped electrode pair are a source electrode and a drain electrodes, a top gate is connected to a bottom of the each U-shaped electrode pairs, and a surface gate, parallel to the top gate and not connected to the each U-shaped electrode pair, is provided within the each U-shaped electrode pair;

the source electrode and the drain electrode are each in turn made up of a silicon layer, an oxidation layer and a metal layer above the ion implantation layer;

silicon nanowires are connected to the source electrode and the drain electrode at the bottom of the each U-shaped electrode pair; each silicon nanowire is constructed by ultraviolet lithography and NLD etching; the each silicon nanowire has a length ranging from 10 nm to 100 µm, a width ranging from 10 nm to 5 µm, and a thickness ranging from 10 nm to 500 µm;

the source electrode, the drain electrodes, the surface gate and the top gate of the each U-shaped electrode pair are all wrapped with a passivation layer, and only ends of the source electrode, the drain electrodes, the surface gate, the top gate and the silicon nanowires are exposed.

2. A preparation method of the biosensor based on a MOS transistor of claim 1, comprising the steps of:
   (I) preparing the detection system;
   (II) preparing the micro-channel system; and
   (III) bonding the detection system and the micro-channel system.

3. The preparation method according to claim 2, wherein step (I) comprises the following procedures:
   a) surface silicon thinning: cleaning a silicon wafer, and performing high-temperature oxidation at 900-1100° C. for 1-10 hours in an oxidation furnace by dry oxidation-wet oxidation-dry oxidation on the silicon wafer; then rinsing with a buffered oxide etch (BOE) to remove a $SiO_2$ layer of the silicon wafer, and reducing the surface silicon of the silicon wafer to 10-100 nm to obtain a silicon-on-insulator (SOI) silicon wafer with a silicon layer;
   b) preparation of silicon nanowires: exposing and developing by an ultraviolet stepper aligner to obtain a nanowire pattern, plating a layer of chromium with a thickness of 10-1000 nm as a mask on a pattern region of the nanowire pattern by magnetron sputtering, and etching integrally by an NLD etching method to remove Si and $SiO_2$ in a non-pattern region and expose the substrate;
   c) ion implantation: performing full-layer ion implantation to conduct the substrate exposed for a later lead-out of the surface gate; wherein, implanted ions in the full-layer ion implantation are nitrogen, phosphorus or arsenic, with an implantation dose of $1e14-1e20/cm^2$, and an implantation energy of 10 keV-1 MeV, to obtain an ion implantation layer;
   d) construction of the oxidation layer on the silicon nanowire: growing $SiO_2$ with a thickness of 1-100 nm on a partial region of the silicon nanowire ultraviolet lithography device and a plasma enhanced chemical vapor deposition (PECVD), for a later lead-out of the top gate;
   e) preparation of patterns of the source electrode, the drain electrode, the surface gate and the top gate: uniformly coating a layer of photoresist on a surface of the SOI silicon wafer, preparing the patterns of the source electrode, the drain electrode, the surface gate and the top gate at specific positions by an ultraviolet lithography method, depositing three metal layers including a first Ti metal layer, an Au metal layer and a second Ti metal layer on the surface of the substrate by thin film deposition techniques, and finally stripping to obtain the patterns; wherein the first Ti metal layer has a thickness of 1-10 nm, the Au metal layer has a thickness of 10-200 nm, and the second Ti metal layer has a thicknesses of 1-10 nm;
   f) preparation of an ohmic contact: rapidly raising a temperature to 350-500° C. with a rapid annealing furnace under a protection of nitrogen, maintaining for 1-100 seconds and then lowering the temperature to establish the ohmic contact between the source electrode or the drain electrode, and the silicon nanowire; and
   g) preparation of the passivation layer: uniformly coating a layer of an electron beam photoresist on the surface of the SOI silicon wafer of the substrate, preparing the passivation layer by an ultraviolet lithography method, and depositing a double-layered thin film including a $SiO_2$ film and a $SiN_x$ film on the surface of the substrate by thin film deposition techniques to obtain the passivation layer in combination with a peel-off technique; wherein the $SiO_2$ film has a thickness of 10-1000 nm and the $SiN_x$ film has a thickness of 10-500 nm.

4. The preparation method according to claim 2, wherein, step (II) comprises the following procedures:
   successively applying ultrasonic cleaning to a silicon wafer with acetone, isopropanol and ultrapure water, respectively, each for 5-15 minutes, coating a layer of photoresist on a surface of the silicon wafer by a glue leveling platform, with a coating thickness of 2-10 µm, obtaining a micro-channel photoresist pattern by performing a ultraviolet lithography on the silicon wafer; and etching on the silicon wafer by deep silicon etching, with an etching depth of 100-150 µm;

performing a fluorosilane treatment on the silicon wafer to make the surface possess superhydrophobic property for facilitating subsequent peel-off of micro-channel materials; coating polydimethylsiloxane (PDMS) or SU-8 photoresist on the surface of the silicon wafer and performing a curing treatment; and peeling the PDMS or SU-8 photoresist off the surface of the silicon wafer after curing;

punching on a surface of the PDMS or the SU-8 photoresist with a puncher to obtain an inlet and an outlet of a micro-channel of the micro-channel system, wherein a region between the inlet and the outlet is a passage in the micro-channel system.

5. The preparation method according to claim 2, wherein, step (III) comprises the following procedures:

performing a surface treatment on the substrate of the micro-channel system and the detection system with an oxygen plasma system to obtain a superhydrophilic surface, and then aligning and bonding the micro-channel system and the detection system to complete a preparation of the biosensor.

6. The biosensor according to claim 1, wherein, a material of a micro-channel in the micro-channel system is polydimethylsiloxane (PDMS) or SU-8 photoresist.

7. A method of detecting a tumor marker using the biosensor according to claim 1, comprising the following steps of:

a) modifying an antibody protein: connecting a micro-channel passage, passing and residing 1-1000 μg/ml of the antibody protein at room temperature by means of a syringe pump or a peristaltic pump on a surface of the silicon nanowire for a modification, wherein a modification time of the modification is less than 0.1 hour to 10 hours; and subsequently cleaning the biosensor with immunostaining washings/a phosphate buffered saline Polysorbate 20 (PBST) solution and blowing to dry the biosensor with nitrogen, wherein a purpose of step a) is to modify the antibody protein corresponding to a target tumor marker on the silicon nanowire of the biosensor;

b) analyzing: after fixing, pricking and passage-connecting operations are completed on a probe station, passing a phosphate buffered saline (PBS) solution through a micro-channel system for 1 minute to 100 minutes at a flow rate of 0.001-100 ml/min by the means of the syringe pump or the peristaltic pump to obtain a base current value as a baseline, and then slowly conveying a sample to be detected to a silicon nanowire region of the biosensor and staying for several minutes, and the target tumor marker in the sample to be detected is sufficiently bound with the antibody protein, and continuously conveying the sample to an outlet of the micro-channel by the means of the syringe pump or the peristaltic pump; and c) detecting: during conveying the sample, capturing, by an electrical analyzer using a C-V mode, changes in electrical signals relative to a baseline indicating presence of the tumor marker in the sample.

8. The method according to claim 7, wherein, the target tumor marker is α-fetoprotein AFP or a carcinoembryonic antigen (CEA) tumor marker.

* * * * *